United States Patent
LaBrenz et al.

(10) Patent No.: US 12,303,483 B2
(45) Date of Patent: May 20, 2025

(54) LIPASE DEGRADATION RESISTANT SURFACTANTS FOR USE IN LARGE MOLECULE THERAPEUTIC FORMULATIONS

(71) Applicant: Janssen Biotech, Inc., Horsham, PA (US)

(72) Inventors: Steven LaBrenz, Exton, PA (US); Patrick Stahl, Exton, PA (US)

(73) Assignee: Janssen Biotech, Inc., Horsham, PA (US)

( * ) Notice: Subject to any disclaimer, the term of this patent is extended or adjusted under 35 U.S.C. 154(b) by 39 days.

(21) Appl. No.: 17/734,523

(22) Filed: May 2, 2022

(65) Prior Publication Data

US 2022/0265596 A1 Aug. 25, 2022

Related U.S. Application Data

(63) Continuation of application No. 16/547,237, filed on Aug. 21, 2019, now abandoned.

(60) Provisional application No. 62/721,884, filed on Aug. 23, 2018.

(51) Int. Cl.
*A61K 31/25* (2006.01)
*A61K 38/46* (2006.01)

(52) U.S. Cl.
CPC ............ *A61K 31/25* (2013.01); *A61K 38/465* (2013.01); *C12Y 301/01001* (2013.01)

(58) Field of Classification Search
CPC .................. A61K 31/35; A61K 38/465; C12Y 301/01001
See application file for complete search history.

(56) References Cited

U.S. PATENT DOCUMENTS

| | | | |
|---|---|---|---|
| 5,418,147 A | 5/1995 | Huang et al. | |
| 5,656,272 A | 8/1997 | Le et al. | |
| 5,770,198 A | 6/1998 | Coller et al. | |
| 6,902,734 B2 | 6/2005 | Giles-Komar et al. | |
| 7,241,733 B2 | 7/2007 | Heavner et al. | |
| 7,935,344 B2 | 5/2011 | Benson et al. | |
| 9,518,128 B2 | 12/2016 | Huntington et al. | |
| 9,605,082 B2 | 3/2017 | Huntington et al. | |
| 9,695,242 B2 | 7/2017 | Chiu et al. | |
| 2006/0142234 A1 | 6/2006 | Chen et al. | |
| 2011/0223208 A1* | 9/2011 | Hill ..................... | A61K 47/44 424/141.1 |
| 2014/0032203 A1 | 1/2014 | Cutts et al. | |
| 2014/0322203 A1 | 10/2014 | Alavattam et al. | |
| 2015/0239970 A1 | 8/2015 | Bee et al. | |
| 2016/0367663 A1 | 12/2016 | Doshi et al. | |
| 2017/0218092 A1 | 8/2017 | Chiu et al. | |
| 2020/0061015 A1 | 2/2020 | LaBrenz et al. | |

FOREIGN PATENT DOCUMENTS

| | | |
|---|---|---|
| WO | WO 2017/031288 A1 | 2/2017 |
| WO | WO 2018/096445 A1 | 5/2018 |

OTHER PUBLICATIONS

PCT International Search Report dated Dec. 3, 2019.
Chiu et al., "Knockout of a Difficult-to-Remove CHO Host Cell Protein, Lipoprotein Lipase, for Improved Polysorbate Stability in Monoclonal Antibody Formulations," *Biotech. Bioeng.* 114(5): 1006-1015 (2017).
Ehnholm et al., "Two Methods Compared for Measuring Lipase Activity in Plasma after Heparin Administration," *Clin. Chem.* 30(9): 1568-70 (1984).
Hernandez-Garcia et al., "An Improved Method to Measure Lipase Activity in Aqueous Media," *Anal. Biochem.* 530:104-106 (2017).
John, G. T., and Heinzle, E., "Quantitative screening method for hydrolases in microplates using pH indicators: determination of kinetic parameters by dynamic pH monitoring", *Biotechnol. Bioeng.* 72(6), pp. 620-627 (2001).
Kerwin BA, "Polysorbates 20 and 80 Used in the Formulation of Protein Biotherapeutics: Structure and Degradation Pathways," *J. Pharm. Sci.* 97(8): 2924-35 (2008).
LaBrenz SR, "Ester Hydrolysis of Polysorbate 80 in mAb Drug Product: Evidence in Support of the Hypothesized Risk After the Observation of Visible Particulate in mAb Formulations," *J. Pharm. Sci.*, 103:2268-2277 (2014).
Tietz and Repique, "Proposed Standard Method for Measuring Lipase Activity in Serum by a Continuous Sampling Technique," *Clin. Chem.* 19(11):1268-1275 (1973).
Valkova, N., et al., "Purification and characterization of PrbA, a new esterase from Enterobacter cloacae</I> hydrolyzing the esters of 4-hydroxybenzoic acid (Parabens)", *J. Biol. Chem.* 278(15), pp. 12779-12785 (2003).
Gennaro, Alfonso R., "Remington's Pharmaceutical Sciences", Mack Publishing Company, 18th Edition, 1990.
Troy et al., "Remington: The Science and Practice of Pharmacy", Lippincott Williams & Wilkins, 21st Edition, 2006.
Hall et al., "Polysorbates 20 and 80 Degradation by Group XV Lysosomal Phospholipase A2 Isomer X1 in Monoclonal Antibody Formulations", vol. 105, No. 5, pp. 1633-1642, May 2016.

\* cited by examiner

*Primary Examiner* — Tekchand Saidha

(57) ABSTRACT

The present invention is directed to pharmaceutical formulations of therapeutic proteins that comprise one or more polyethoxylated fatty alcohol (PFA) surfactants that are resistant to lipase mediated degradation. The present invention is also directed to methods of reducing aggregate and/or particulate formation in pharmaceutical formulations of therapeutic proteins and methods of maintaining a stable surfactant level in pharmaceutical formulations of therapeutic proteins.

14 Claims, 8 Drawing Sheets

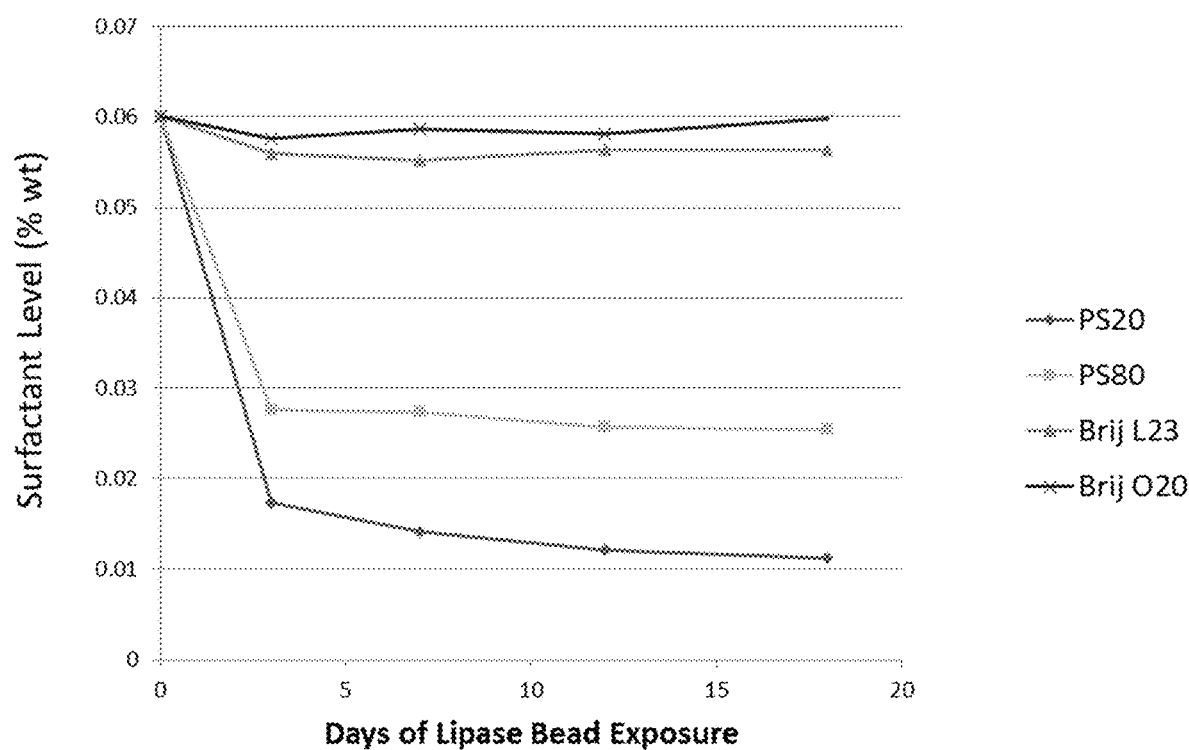

LIPASE DEGRADATION RESISTANT SURFACTANTS FOR USE IN LARGE MOLECULE THERAPEUTIC FORMULATIONS

CROSS-REFERENCE TO RELATED APPLICATIONS

This application is a Continuation of U.S. application Ser. No. 16/547,237, filed 21 Aug. 2019, which claims the benefit of U.S. Provisional Application Ser. No. 62/721,884, filed 23 Aug. 2018. The entire contents of the aforementioned applications are incorporated herein by reference in their entirety.

FIELD OF THE INVENTION

The present invention is directed to pharmaceutical formulations of therapeutic proteins that comprise one or more lipase resistant surfactants. The present invention is also directed to methods of reducing aggregate and/or particulate formation in pharmaceutical formulations comprising therapeutic proteins and extending the shelf-life of such pharmaceutical formulations.

BACKGROUND OF THE INVENTION

The inclusion of surfactants in large molecule formulations is a commonly used strategy for stabilizing the biological molecules, preventing adherence to surfaces, avoiding turnover at the air-water interface, protecting against surface-induced denaturation, and limiting self-association events that would otherwise lead to aggregation. Protein aggregation can occur during drug processing, long term storage, shipment, and during administration. However, the addition of a surfactant has been shown to minimize interfacial interactions that may stress proteins during filtration, agitation, freeze-thaw, lyophilization, reconstitution, administration, and storage. Currently, the dominant surfactants used by the pharmaceutical industry in large molecule commercial formulations are polysorbates, e.g., polysorbate 20 (PS20) and polysorbate 80 (PS80). Each of these surfactants has their advantages, e.g., they decrease protein self-association at an interface and prevent protein aggregation. However, a primary disadvantage of their use relates to their oxidative degradation (Kerwin B A, "Polysorbates 20 and 80 Used in the Formulation of Protein Biotherapeutics: Structure and Degradation Pathways," *J. Pharm. Sci.* 97(8): 2924-35 (2008), which is hereby incorporated by reference in its entirety) and catalytic degradation (LaBrenz S R, "Ester Hydrolysis of Polysorbate 80 in mAb Drug Product: Evidence in Support of the Hypothesized Risk After the Observation of Visible Particulate in mAb Formulations," *J. Pharm. Sci.*, 103:2268-2277 (2014), which is hereby incorporated by reference in its entirety), which, in turn, negatively impacts the stability and shelf-life of large molecule formulations.

Oxidative degradation of polysorbates can be mitigated in protein formulations by co-formulating with antioxidants (e.g., methionine) or with tryptophan (see, e.g., U.S. Patent Application Publication Nos. 2014/0322203 to Alavattam et al.). However, the enzymatic degradation of polysorbates, which has been attributed to the presence of host cell lipases and esterases (LaBrenz S R, "Ester Hydrolysis of Polysorbate 80 in mAb Drug Product: Evidence in Support of the Hypothesized Risk After the Observation of Visible Particulate in mAb Formulations," *J. Pharm. Sci.*, 103:2268-2277 (2014)), remains a significant challenge to biopharmaceutical development. While purification processes exist to remove host cell proteins (HCPs), such processes are often inadequate at removing all HCPs and they are typically cost prohibitive to implement at the manufacturing level. As a result, trace quantities of certain host cell proteins, including some lipases, are typically retained in biopharmaceutical products (Chiu et al., "Knockout of a Difficult-to-Remove CHO Host Cell Protein, Lipoprotein Lipase, for Improved Polysorbate Stability in Monoclonal Antibody Formulations," *Biotech. Bioeng.* 114(5): 1006-1015 (2017)). Thus, there is a need in the art for the identification of surfactants that possess the advantageous properties of polysorbate surfactants without some of the disadvantages related to degradation, i.e., effective at preventing protein aggregation and protein turnover, but resistant to host cell protein mediated degradation.

The present invention is directed at overcoming the deficiencies in the art related to host cell protein mediated degradation of surfactants in large molecule formulations.

SUMMARY OF THE INVENTION

A first aspect of the present invention is directed to a pharmaceutical formulation. The pharmaceutical formulation of the present invention comprises about 20 mg/mL to about 200 mg/mL of a therapeutic protein, a pharmaceutically acceptable carrier, and one or more polyethoxylated fatty alcohol (PFA) surfactants, where the one or more PFA surfactants is resistant to lipase degradation Another aspect of the present invention is directed to a method of reducing aggregate and/or particulate formation in a pharmaceutical formulation that comprises a biological composition. This method involves providing a biological composition, where the biological composition comprises about 20 mg/mL to about 200 mg/mL of therapeutic protein and incorporating one or more lipase resistant polyethoxylated fatty alcohol (PFA) surfactants in the biological composition as a replacement for a polysorbate surfactant.

Another aspect of the present invention is directed to a method of extending the shelf life of a pharmaceutical formulation that comprises a biological composition. This method involves providing a biological composition, where the biological composition comprises about 20 mg/mL to about 200 mg/mL of therapeutic protein, and incorporating one or more lipase resistant polyethoxylated fatty alcohol (PFA) surfactants in the biological composition as a replacement for a polysorbate surfactant.

Another aspect of the present invention is directed to a method of producing a pharmaceutically acceptable therapeutic protein formulation comprising a stable surfactant concentration. This method involves providing a pharmaceutically acceptable therapeutic protein composition and incorporating one or more lipase resistant polyethoxylated fatty alcohol (PFA) surfactants in the therapeutic protein composition, thereby producing a pharmaceutically acceptable therapeutic formulation comprising a surfactant concentration that remains stable over the shelf life of the formulation.

Polysorbates are currently the standard surfactant used by the pharmaceutical industry. However, degradation of polysorbate can occur in large molecule formulations as a result of residual host cell protein impurities, namely lipases. The decrease of intact polysorbate levels over time, together with the formation of polysorbate degradant particles (e.g., free fatty acids) and large molecule destabilizing polysorbate degradants, lead to formulation instability, reduced drug product shelf life, longer development timelines, and more frequent manufacturing campaigns, all of which reduce patient access to therapeutic molecules. As demonstrated herein, it was unexpectedly found that polyethoxylated fatty alcohol (PFA) surfactants function to stabilize biotherapeutics the same as, and in some cases better than, their counterpart polysorbate surfactants, e.g., polysorbate 20 and polysorbate 80. Unlike polysorbate surfactants, PFAs are resistant to degradation by host cell lipases; therefore, the concentration of the PFA surfactant remains stable in the formulation overtime and able to protect the therapeutic molecule of the formulation from aggregation and particulate formation. As a result, the stability of the therapeutic molecule formulation is significantly improved as compared to a corresponding therapeutic molecule formulation containing polysorbate surfactant when the surfactants are exposed to lipases.

BRIEF DESCRIPTION OF THE DRAWINGS

FIG. 2 is a graph showing surfactant level (% w/v) in stock solutions exposed to lipases immobilized on beads over the course of 18 days. The levels of intact polysorbate 20 (PS20) and polysorbate 80 (80) declined significantly over the course of exposure, whereas the levels of PFA surfactants (i.e., Brij® 020 and Brij® L23) remained relatively constant.

FIG. 4A shows the DLS results for bispecific mAb A, FIG. 4B shows the DLS results for bispecific mAb B, and FIG. 4C shows the DLS results for IgG4 mAb C.

DETAILED DESCRIPTION OF THE INVENTION

Figure 1A:
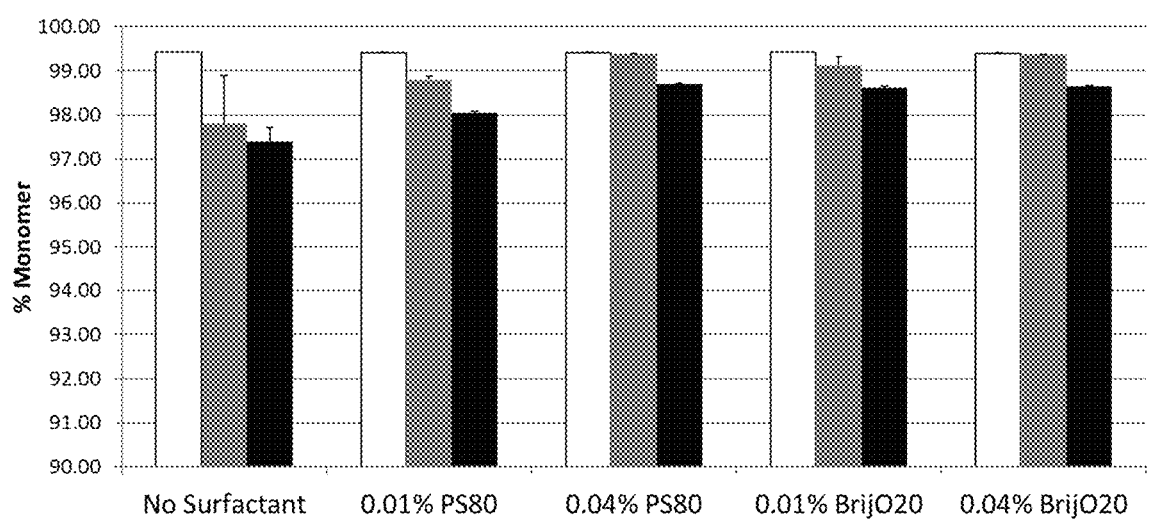
FIGS. 1A-1C are graphs showing the protective effect of polysorbate surfactants (i.e., polysorbate 20 (PS20) and polysorbate 80 (PS80)) and polyethoxylated fatty alcohol (PFA) surfactants (i.e., Brij® 020 and Brij® L23) on antibody stability after exposure to shaking or thermal stress as measured by size exclusion chromatography (SEC). The graphs show percent monomer present in each formulation at time zero (T0; white bar), after shaking stress (72 hours of shaking at 250 RPM at ambient temperature; grey bars), and after thermal stress (3 month incubation at 25° C., followed by shaking stress of 72 h at 250 RPM; black bars). Three different antibody formulations were tested including bispecific mAb A (FIG. 1A), bispecific mAb B (FIG. 1B), and IgG4 mAb C (FIG. 1C). Details of antibody formulations are described herein in the Examples.

A first aspect of the present invention is directed to a pharmaceutical formulation. The pharmaceutical formulation of the present invention comprises about 20 mg/mL to about 200 mg/mL of a therapeutic protein, a pharmaceutically acceptable carrier, and one or more polyethoxylated fatty alcohol (PFA) surfactants, where the one or more PFA surfactants is resistant to lipase degradation.

The "pharmaceutical formulation" of the present invention is a preparation which is in a form that permits the biological activity of the active ingredient to be effective, and which contains no additional components that are unacceptably toxic to a subject to which the formulation is administered.

In accordance with this aspect of the present invention, the pharmaceutical formulation is a biopharmaceutical formulation comprising a therapeutic protein. A "therapeutic protein" as used herein encompasses any therapeutic product made of two or more coupled amino acids. Therapeutic proteins include non-recombinant, serum isolated proteins and peptide or polypeptide fragments thereof, recombinant proteins and peptide or polypeptide fragments thereof, antibodies and antigen binding portions thereof, and antibody mimetics. Therapeutic proteins also include recombinant and non-recombinant fusion proteins and peptides, chimeric proteins and peptides, and protein and peptide conjugates, and well as antibody and antibody fragment fusions (e.g., Fc fusion protein), chimeras, and conjugates. Therapeutic proteins also include engineered protein scaffolds, e.g., fibronectin type III domain scaffold binding proteins or monobodies.

In one embodiment, the therapeutic protein is an antibody. Antibodies include both full length antibodies, antigen binding fragments thereof, and antibody derivatives. Suitable antibodies include polyclonal and monoclonal antibodies of any class (e.g., IgG, IgE, IgM, IgD, and IgA), and any subclass (e.g., IgG1, IgG2, IgG3, IgG4, IgA1 and IgA2). The antibody can be a humanized antibody, a human antibody, a chimeric antibody, a CDR-grafted antibody, a multispecific antibody (e.g., bi-specific or tri-specific antibodies). Suitable antibody fragments include, without limitation, any molecule containing an antigen binding region or antigen binding domain of a full antibody, e.g., single domain antibodies comprising the heavy chain variable region ($V_H$) or the light chain variable region ($V_L$). In one embodiment, the antibody fragment comprises a single-chain polypeptide containing a portion of the light-chain variable domain (e.g., one, two or three of the complementary determining regions (CDRs)), or a single-chain polypeptide containing a portion of the heavy chain variable domain. Other suitable antibody fragments encompassed by the present invention include antigen-binding (F(ab)) fragments and F(ab')2 fragments.

In another embodiment, the therapeutic protein is an antibody derivative. Antibody derivatives include, for example and without limitation, single-chain antibodies (scFv), tandem scFvs, diabodies, triabodies, or linear antibodies.

Exemplary therapeutic antibodies of the pharmaceutical formulation as described herein include, without limitation, the anti-TNF-α/IL-17A duobody CNTO 9762 (U.S. Patent Application Publication No. 20170218092 to Chiu et al., which is hereby incorporated by reference in its entirety); the anti-CD38 antibody Daratumumab (U.S. Patent Application Publication No. 20160367663 to Doshi et al., which is hereby incorporated by reference in its entirety); the anti-thrombin antibody Ichorcumab (U.S. Pat. Nos. 9,518,128 and 9,605,082 to Huntington et al, which are hereby incorporated by reference in their entirety); the anti-EGFR/c-Met duobody CNTO 4424 (U.S. Pat. No. 9,695,242 to Chiu et al., which is hereby incorporated by reference in its entirety); the anti-IL23 antibody Guselkumab (CNTO-1959) (U.S. Pat. No. 7,935,344 to Benson et al, which is hereby incorporated by reference in its entirety); the anti-IL12 antibody Ustekinumab (Stelara®) (U.S. Pat. No. 6,902,734 to Giles-Komar et al, which is hereby incorporated by reference in its entirety); erythropoietin (EPO)-mimetic peptide antibody fusion proteins CNTO 528 or CNTO 530 (U.S. Pat. No. 7,241,733 to Heavner et al., which is hereby incorporated by reference in its entirety); the anti-TNFα antibody infliximab (U.S. Pat. No. 5,656,272 to Le et al., which is hereby incorporated by reference in its entirety); and the platelet-specific antibody Abciximab (U.S. Pat. No. 5,770,198 to Coller et al., which is hereby incorporated by reference in its entirety).

The concentration of the therapeutic protein in the pharmaceutical formulation will vary depending upon numerous factors including, without limitation, the activity of the therapeutic protein, the condition being treated, the age of the intended recipient population, route of administration, among other things. Thus, the pharmaceutical formulation of the present invention comprises a concentration of a therapeutic protein in the range from about 10 mg/mL to about 250 mg/mL or any range between these values. In some embodiments, the therapeutic protein is at a concentration greater than about 250 mg/mL. In some embodiments, the therapeutic protein is at a concentration in the range from any one of about 10 mg/mL to 250 mg/mL, 50 mg/mL to 250 mg/mL, 100 mg/mL to 250 mg/mL, 150 mg/mL to 250 mg/mL, 200 mg/mL to 250 mg/mL, 10 mg/mL to 200 mg/mL, 20 mg/mL to 200 mg/mL, 50 mg/mL to 200 mg/mL, 100 mg/mL to 200 mg/mL, 150 mg/mL to 200 mg/mL, 10 mg/mL to 150 mg/mL, 50 mg/mL to 150 mg/mL, 100 mg/mL to 150 mg/mL, 10 mg/mL to 100 mg/mL, 50 mg/mL to 100 mg/mL, 10 mg/mL to 50 mg/mL or any range between these ranges.

In accordance with this aspect of the present invention, the therapeutic protein of the pharmaceutical formulation is one that is produced from a biological source, e.g., a primary population of cells or an immortalized cell line. In one embodiment, the therapeutic protein is produced in a mammalian cell line. Suitable mammalian cell lines include hamster cell lines such as Chinese Hamster Ovary (CHO) cell lines CHODG44 and DUXB11 (Gibco, Gaithersburg, MD), CHO-K1 (American Type Culture Collection (ATCC) #CCL-61), CHO-S (Gibco), Freestyle CHO-S (Invitrogen, Carlsbad, CA), CHO-T (Acyte, Brisbane, Australia), and CHO3E7 (National Research Council of Canada (CNRC) #L-11992). Suitable mammalian cell lines also include mouse cell lines, e.g., the mouse myeloma NS0 cell line (European Collection of Authenticated Cell Cultures (ECACC) #85110503) and mouse myeloma cell line Sp2/0 (ATCC-CRL-1581). Suitable mammalian cells also include human cell lines such as human amniocyte, e.g., CAP cells and CAP-T cells (Cevec, Koln, Germany), human retina cells, e.g., PER.C6 cells (Crucell, Leiden, Netherlands), or human embryonic kidney cells, e.g., Freestyle HEK2930F cells (Invitrogen), HEK 293 6E (CNRC #L-11266), HEK 293 T (ATCC #CRL-11268).

The lipase or esterase activity in the pharmaceutical formulation as described herein will vary depending upon numerous factors including, without limitation, the concentration of the therapeutic protein, the biological source of the therapeutic protein, and methods of therapeutic protein purification employed. In one embodiment, the lipase activity in the pharmaceutical formulation is ≥1 unit/mL of purified porcine esterase or equivalent thereof, where one "unit" of lipase/esterase activity hydrolyzes 1.0 μmole of ethyl butyrate to butyric acid and ethanol per minute at pH 8.0 at 25° C.

The pharmaceutical formulation of the present invention also comprises one or more polyethoxylated fatty alcohol (PFA) surfactants. The incorporation of one or more PFA surfactants is particularly advantageous in pharmaceutical formulations containing a therapeutic protein that was produced in a biological system, like a cell, because PFAs are resistant to degradation by residual host cell proteins that are carried over to the formulation. In particular, PFAs are resistant to host cell lipases that cannot be adequately removed from the therapeutic protein preparation, and which are highly active at very low concentrations.

PFAs (also referred to as alcohol ethoxylates) encompass a class of non-ionic surfactants that contain a hydrophobic alkyl chain attached via an ether linkage to a hydrophilic ethylene oxide (EO) chain. This class of surfactants is defined by a general structure of Formula I.

R(OCH$_2$CH$_2$)$_n$OH                          Formula I

The alkyl chain, R, of the PFA varies in length and degree of linearity, but is typically between 8 and 18 carbons in length, in some embodiments, between 11-15 carbons in length. The length of the EO chain (i.e., n of formula I) also varies in length from about 1 to about 40 EO units. In one embodiment, the PFA of the pharmaceutical formulation of the present invention comprises a PFA having an ethylene oxide chain comprising about 5 to about 40 ethylene oxide units (i.e., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 38, 39, or 40 EO units).

While PFAs are surfactants that are used primarily in laundry detergents and other household products, PFAs have not been used in pharmaceutical formulations of biologic molecules, in particular, pharmaceutical formulations comprising therapeutic proteins, such as antibodies. However, as demonstrated herein, it was unexpectedly found, that this class of surfactants function the same as, and in some cases better than polysorbate surfactants, e.g., polysorbate 20 and polysorbate 80, which are the predominant surfactants utilized by the pharmaceutical industry in large molecule commercial formulations. Unlike polysorbate surfactants, PFAs are resistant to degradation by host cell lipases; therefore, the concentration of the PFA surfactant remains stable in the formulation overtime and able to protect the therapeutic protein of the formulation from aggregation and particulate formation. As a result, the stability of the therapeutic protein formulation is significantly improved as compared to a corresponding therapeutic protein formulation containing polysorbate surfactant when the surfactants are exposed to lipases.

In one embodiment, the pharmaceutical formulation of the present invention comprises a polyoxyethylene lauryl ether (CAS No. 9002-92-0). Exemplary polyoxyethylene lauryl ethers include, without limitation, polyoxyethylene

(23) lauryl ether (also known by the tradenames Brij® L23 and Brij® 35); polyoxyethylene (4) lauryl ether (also known as polyethylene glycol dodecyl ether and Brij® L4); and polyoxyethylene (10) lauryl ether (also known as decaethylene glycol monododecyl ether).

In another embodiment, the pharmaceutical formulation of the present invention comprises a polyoxyethylene oleyl ether (CAS No. 9004-98-2). Exemplary polyoxyethylene oleyl ethers include, without limitation, polyoxyethylene (20) oleyl ether (also know by the tradenames Brij® 98, Brij® 99, and Brij® 020); polyoxyethylene (10) oleyl ether (also know by the tradenames Brij® 010 and Brij® 97); and polyoxyethylene (2) oleyl ether (also know by the tradenames Brij® 93 and polyethylene glycol oleyl ether).

In another embodiment, the pharmaceutical formulation of the present invention comprises a polyoxyethylene stearyl ether (Cas No. 9005-00-9). Exemplary polyoxyethylene stearyl ethers include, without limitation, polyoxyethylene (20) stearyl ether (also know by the tradename Brij® S20); polyoxyethylene (100) stearyl ether (also known by the tradename Brij® S100); polyoxyethylene (10) stearyl ether (also known by the tradenames Brij® S10 and polyethylene glycol octadecyl ether); and polyoxyethylene (2) stearyl ether (also known by the tradename Brij® S2).

In another embodiment, the pharmaceutical formulation of the present invention comprises a polyoxyethylene cetyl ether (Cas No. 9004-95-9). Exemplary polyoxyethylene cetyl ethers include, without limitation, polyoxyethylene (20) cetyl ether (also known by the tradenames Brij® 58 and polyethylene glycol hexadecyl ether); polyoxyethylene (2) cetyl ether (also known by the tradename Brij® 52); and polyoxyethylene (10) cetyl ether (also known by the tradename Brij® C10).

In one embodiment, the pharmaceutical formulation of the present invention comprises about 0.001% to about 0.4% (w/v) of PFA surfactant. In one embodiment, the pharmaceutical formulation comprises about 0.005% to about 0.2% (w/v) of the PFA surfactant. In one embodiment, the pharmaceutical formulation comprises about 0.01% to about 0.1% (w/v) of PFA surfactant (i.e., about 0.01%, 0.02%, 0.03%, 0.04%, 0.05%, 0.06%, 0.07%, 0.08%, 0.09%, 0.1%). In another embodiment, the pharmaceutical formulation comprises about 0.01% to about 0.09% (w/v) of PFA surfactant. In another embodiment, the pharmaceutical formulation comprises about 0.01% to about 0.06% (w/v) of PFA surfactant. In another embodiment, the pharmaceutical formulation comprises about 0.01% to about 0.04% (w/v) of PFA surfactant.

The pharmaceutical formulation of the present invention is a stable formulation. As referred to herein, a "stable formulation" is one in which the protein therein essentially retains its physical stability and/or chemical stability and/or biological activity upon storage. Preferably, the formulation essentially retains its physical and chemical stability, as well as its biological activity upon storage. Steady levels of PFA surfactant during processing and storage contribute to the stability of the formulations describe herein. In one embodiment, the formulation retains 70% of its starting level of PFA under appropriate storage conditions. In another embodiment, the formulation retains 75%, 80%, 85%, 90%, 91%, 92%, 93%, 94%, 95%, 96%, 97%, 98%, 99%, or 100% of its starting level of PFA surfactant under appropriate storage conditions.

In some embodiments, >90% of the PFA remains intact after the formulation is stored at about 1° C. to about 10° C. for about six months, at least about 12 months, at least about 18 months, at least about 24 months, at least about 30 months, at least about 36 months, at least about 42 months, or at least about 48 months.

In some embodiments, >95% of the PFA remains intact in the formulation after the formulation is stored at about 1° C. to about 10° C. for at least about six months, at least about 12 months, at least about 18 months, at least about 24 months, at least about 30 months, at least about 36 months, at least about 42 months, or at least about 48 months.

In another embodiment, >90% of the PFA remains intact after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months. In some embodiments, >95% of the PFA remains intact after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months.

In another embodiment, >90% of the PFA remains intact after the formulation is stored at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months. In some embodiments, >95% of the PFA remains intact after the formulation is stored at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months.

Various analytical techniques known in the art can be utilized for measuring protein stability in the pharmaceutical formulations of the present invention. Stability can be measured at a selected amount of light exposure and/or temperature for a selected time period. Stability can be evaluated qualitatively and/or quantitatively in a variety of different ways, including evaluation of aggregate formation. Aggregate formation can be evaluated by, for example and without limitation, size exclusion chromatography, turbidity, and/or by visual inspection. Stability can also be evaluated based on particulate and sub-visible particulate formation, which can be assessed using, for example and without limitation, dynamic light scattering, nanoparticle tracking analysis, resonant mass measurement, light obscuration, and flow imaging. In another embodiment, stability is measured by evaluation of ROS formation, using for example and without limitation, a light stress assay or a 2,2'-Azobis(2-Amidinopropane) Dihydrochloride (AAPH) stress assay. In another embodiment, stability is assessed based on the oxidation of specific amino acid residues of the protein. This analysis can be carried out using antibody detection. For example, detection of a Trp residue and/or a Met residue by monoclonal antibody detection. In another embodiment, stability is evaluated by assessing charge heterogeneity using cation exchange chromatography, image capillary isoelectric focusing (icIEF) or capillary zone electrophoresis. Other measures of stability that are suitable for use in accordance with the methods described herein include, without limitation, amino-terminal or carboxy-terminal sequence analysis; mass spectrometric analysis; SDS-PAGE or capillary electrophoresis SDS analysis to compare reduced and intact antibody; peptide map (for example tryptic or LYS-C) analysis; and evaluating biological activity or target binding function of the protein (e.g., antigen binding function of an antibody.

In one embodiment the pharmaceutical formulation of the present invention has enhanced stability as compared to pharmaceutical formulations comprising the same therapeutic protein but formulated with a polysorbate surfactant. In one embodiment, the stability of the pharmaceutical formulation of the present invention is characterized by the percentage of therapeutic protein in the formulation that maintains its desired monomeric state (vs. a dimer or trimer aggregated state). Accordingly, in one embodiment, >90% of the therapeutic protein in the pharmaceutical formulation comprising a PFA surfactant as described herein is in a monomeric state for its shelf-life. In another embodiment, at least 91%, 92%, 93%, 94%, 95%, 96%, 97%, 98%, 99% of the therapeutic protein in the pharmaceutical formulation is in the desired monomeric state for the entirety of its shelf-life.

In another embodiment, >90% of the therapeutic protein is in a monomeric state after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months. In another embodiment, >95% of the therapeutic protein is in a monomeric state after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months.

In another embodiment, >90% of the therapeutic protein is in a monomeric state after the formulation is stored at about 1° C. to about 10° C. for about six months, at least about 12 months, at least about 18 months, at least about 24 months, at least about 30 months, at least about 36 months, at least about 42 months, or at least about 48 months. In some embodiments, >95% of the therapeutic protein is in a monomeric state after the formulation is stored at about 1° C. to about 10° C. for at least about six months, at least about 12 months, at least about 18 months, at least about 24 months, at least about 30 months, at least about 36 months, at least about 42 months, or at least about 48 months.

In another embodiment, >90% of the therapeutic protein is in a monomeric state after the formulation is stored at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months. In another embodiment, >95% of the therapeutic protein is in a monomeric state after the formulation is stored at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months.

In another embodiment, the formulation of the present invention is a stable formulation, as shown by its resistance to sub-visible particulate formation. In one embodiment, the formulations as described herein contain ≤6000 particles (≥10 μm in size) per container (e.g., 1 mL to 50 mL vial or 0.25 mL to 2 mL syringe) and ≤600 particles (≥25 μm in size) per container after storage at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months.

In another embodiment, the therapeutic protein pharmaceutical formulations described herein are resistance to sub-visible particulate formation during cold storage. In one embodiment, the formulations as described herein contain ≤6000 particles (≥10 μm in size) per container and ≤600 particles (≥25 μm in size) per container after storage at about 1° C. to about 10° C. for about six months, at least about 12 months, at least about 18 months, at least about 24 months, at least about 30 months, at least about 36 months, at least about 42 months, or at least about 48 months.

In another embodiment, the therapeutic protein pharmaceutical formulations described herein are resistance to sub-visible particulate formation during long-term cold storage. In one embodiment, the formulations as described herein contain ≤6000 particles (≥10 μm in size) per container and ≤600 particles (≥25 μm in size) per container after storage at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months.

In another embodiment, the therapeutic protein pharmaceutical formulations described herein are stable formulations as demonstrated by their resistance to visible particulate formation. In one embodiment, the formulations as described herein contain ≤80 particles (≥70 μm in size) per milliliter after storage at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months. In another embodiment, the formulations as described herein contain ≤10 particles (≥70 μm in size) per milliliter after storage at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months.

The stable therapeutic protein pharmaceutical formulations as described herein are resistant to visible particulate formation during cold storage. In one embodiment, the formulations as described herein contain ≤80 particles (≥70 μm in size) per milliliter after storage at about 1° C. to about 10° C. for about six months, at least about 12 months, at least about 18 months, at least about 24 months, at least about 30 months, at least about 36 months, at least about 42 months, or at least about 48 months. In another embodiment, the formulations as described herein contain ≤10 particles (≥70 μm in size) per milliliter after storage at about 1° C. to about 10° C. for at least about six months, at least about 12 months, at least about 18 months, at least about 24 months, at least about 30 months, at least about 36 months, at least about 42 months, or at least about 48 months.

In another embodiment, the therapeutic protein pharmaceutical formulations described herein are resistant to visible particulate formation during long-term cold storage. In one embodiment, the formulations as described herein contain ≤80 particles (≥70 μm in size) per milliliter after storage at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months. In another embodiment, the formulations as described herein contain ≤10 particles (≥70 μm in size) per milliliter after storage at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months.

In another embodiment, the stable formulations of the present invention have low turbidity. In one embodiment, the turbidity of the formulations as described herein is ≤18.0 NTU (Nephelometric Turbidity Unit) after storage at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months.

In another embodiment, the stable therapeutic protein pharmaceutical formulations have low turbidity during cold storage. In one embodiment, the turbidity of the formulations as described herein is ≤18.0 NTU after storage at about 1° C. to about 10° C. for about six months, at least about 12 months, at least about 18 months, at least about 24 months, at least about 30 months, at least about 36 months, at least about 42 months, or at least about 48 months.

In another embodiment, the stable therapeutic protein pharmaceutical formulations have low turbidity during cold storage. In one embodiment, the turbidity of the formulations as described herein is ≤18.0 NTU after storage at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months.

The pharmaceutical formulation of the present invention can further comprise at least one of any suitable auxiliary agents, such as, but not limited to, diluents, binders, stabilizers, buffers, salts, lipophilic solvents, preservatives, adjuvants or the like. Non-limiting examples of, and methods of preparing such sterile solutions are well known in the art, see, e.g., Gennaro A R., *Remington's Pharmaceutical Sciences*, 18$^{th}$ ed, Mack Publishing Co. (1990), which is hereby incorporated by reference in its entirety.

Pharmaceutical excipients and additives useful in the present composition include, but are not limited to, proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), myoinositol and the like. The carbohydrate excipient comprises from about 0.5% to about 15% w/v of the pharmaceutical formulation described herein.

The formulation of the present invention can also include a buffer or a pH-adjusting agent. Typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. The buffering salts are typically present in pharmaceutical formulations of the present invention at a concentration of about 5 mM to about 50 mM.

The pH of the formulations can range from about pH 4 to about pH 10, from about pH 5 to about pH 9, or from about pH 6 to about pH 8. In one embodiment, the formulations of the present invention have a pH between about pH 6.8 and about pH 7.8. Preferred buffers include phosphate buffers and sodium phosphate buffers, e.g., phosphate buffered saline (PBS).

Additionally, the pharmaceutical formulation of the present invention can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, lipids (e.g., phospholipids, fatty acids), steroids (e.g., cholesterol), and chelating agents (e.g., EDTA).

The pharmaceutical formulation of the present invention may further comprise one or more pharmaceutically acceptable carriers. A "pharmaceutically acceptable carrier" refers to a diluent, adjuvant, excipient, or vehicle with which the therapeutic protein is formulated with. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration).

The pharmaceutical formulation described herein may also contain pharmaceutically acceptable auxiliary substances as required to approximate physiological conditions such as pH adjusting and buffering agents, stabilizing, thickening, lubricating and coloring agents, etc. The concentration of the therapeutic protein in such pharmaceutical formulations may vary, from less than about 0.5%, usually to at least about 1%, to as much as 15%, 20%, 25%, 30%, or >30% by weight and may be selected primarily based on required dose, fluid volumes, viscosities, etc., according to the particular mode of administration selected. Suitable vehicles and formulations, inclusive of other human proteins, e.g., human serum albumin, are described, for example, in REMINGTON: THE SCIENCE AND PRACTICE OF PHARMACY, 21$^{st}$ Edition, (2006), which is hereby incorporated by reference in its entirety.

Another aspect of the present invention is directed to a method of reducing aggregate and/or particulate formation in a pharmaceutical formulation that comprises a biological composition. This method involves providing a biological composition, where the biological composition comprises about 20 mg/mL to about 200 mg/mL of therapeutic protein, and incorporating one or more lipase resistant polyethoxylated fatty alcohol (PFA) surfactants in the biological composition as a replacement for a polysorbate surfactant.

Another aspect of the present invention is directed to a method of extending the shelf life of a pharmaceutical formulation that comprises a biological composition. This method involves providing a biological composition, where the biological composition comprises about 20 mg/mL to about 200 mg/mL of therapeutic protein, and incorporating one or more lipase resistant polyethoxylated fatty alcohol (PFA) surfactants in the biological composition as a replacement for a polysorbate surfactant.

Another aspect of the present invention is directed to a method of producing a pharmaceutically acceptable therapeutic protein formulation comprising a stable surfactant concentration. This method involves providing a pharmaceutically acceptable therapeutic protein composition and incorporating one or more lipase resistant polyethoxylated fatty alcohol (PFA) surfactants in the therapeutic protein composition thereby, producing a pharmaceutically acceptable therapeutic formulation comprising a surfactant concentration that remains stable over the shelf life of the formulation.

The methods as described herein are particularly suitable for biological compositions having a lipase/esterase activity that is ≥1 unit/mL of purified porcine esterase or equivalent thereof, where one "unit" of activity hydrolyzes 1.0 μmole of ethyl butyrate to butyric acid and ethanol per minute at pH 8.0 at 25° C. It is this level of lipase activity in a biological composition that is sufficient to cause polysorbate degradation, subsequently jeopardizing the stability of the biological composition. Thus, in one embodiment, the methods as described herein involve providing a pharmaceutical formulation of a biological composition, where the biological composition has a lipase/esterase activity of ≥1 units/mL of purified porcine esterase or equivalent thereof. Incorporating the one or more lipase resistance PFA surfactants into this biological composition as a replacement for a polysorbate surfactant will mitigate surfactant degradation over time and reduce aggregate and/or particulate formation in the biological composition and in the pharmaceutical formulation. Such pharmaceutical formulations will have an extended shelf-life and a stable surfactant over the course of the formulation's shelf-life. In certain embodiments, the methods as described herein provide a pharmaceutical formulation of a biological composition with one or more lipase resistance PFA surfactants, wherein the biological composition has a lipase/esterase activity of ≥1 units/mL of purified porcine esterase or equivalent thereof. In certain other embodiments, the methods as described herein provide a pharmaceutical formulation of a biological composition with one or more lipase resistance PFA surfactants, wherein the biological composition has a lipase/esterase activity of ≥1, ≥0.9, ≥0.8, ≥0.7, ≥0.6, ≥0.5, ≥0.4, ≥0.3, ≥0.2, ≥0.1 units/mL of purified porcine esterase or equivalent thereof.

In certain embodiments, the methods as described herein provide a pharmaceutical formulation of a biological composition with one or more lipase resistance PFA surfactants, wherein the biological composition has a lipase/esterase activity of ≥0.1 units/mL of purified porcine esterase or equivalent thereof.

In another embodiment, the methods of the present invention further involve measuring lipase activity of the biological composition prior to incorporating the one or more lipase resistant PFA surfactants. Suitable methods of measuring lipase activity in a biological sample are known in the art, see, e.g., Hernandez-Garcia et al., "An Improved Method to Measure Lipase Activity in Aqueous Media," *Anal. Biochem.* 530:104-106 (2017), Tietz and Repique, "Proposed Standard Method for Measuring Lipase Activity in Serum by a Continuous Sampling Technique," *Clin. Chem.* 19(11):1268-1275 (1973), Ehnholm et al., "Two Methods Compared for Measuring Lipase Activity in Plasma after Heparin Administration," *Clin. Chem.* 30(9): 1568-70 (1984), which are hereby incorporated by reference in their entirety. Generally, a suitable method of measuring lipase activity of the biological sample involves measuring the conversion of 4-nitrophenyl acetate to 4-nitrophenol by the esterase/lipase present in the sample. This conversion can be monitored, detected, and quantified using spectrophotometric methods. For example, at pH>6.0 the conversion the 4-nitrophenol is colored yellow and its production can be monitored at 400 nm. As noted above, a lipase resistant PFA surfactant is incorporated into biological compositions comprising a lipase/esterase activity of ≥1 unit/mL of purified porcine esterase or equivalent thereof.

The methods of the present invention can be employed on pharmaceutical compositions comprising any of the therapeutic proteins described supra, including, without limitation, non-recombinant, serum isolated proteins and peptides thereof, recombinant proteins or peptides thereof, an antibody or an antigen binding portion thereof, antibody derivatives, and/or antibody-drug conjugate.

In accordance with these methods of the present invention, the pharmaceutical formulation comprises a therapeutic protein that is derived from a biological source, i.e., a population of cells or a cell line. Cell lines from which the therapeutic protein may be obtained from include, without limitation, mammalian CHO cell lines, PER.C6 cell lines, and Sp2/0 cell lines as described supra. The concentration of the therapeutic protein in the formulation ranges from about 10 mg/mL to about 250 mg/mL or any range between these values as described supra. In some embodiments, the therapeutic protein is at a concentration greater than about 250 mg/mL. In some embodiments, the therapeutic protein is at a concentration in the range from any one of about 10 mg/mL to 250 mg/mL, 50 mg/mL to 250 mg/mL, 100 mg/mL to 250 mg/mL, 150 mg/mL to 250 mg/mL, 200 mg/mL to 250 mg/mL, 10 mg/mL to 200 mg/mL, 50 mg/mL to 200 mg/mL, 100 mg/mL to 200 mg/mL, 150 mg/mL to 200 mg/mL, 10 mg/mL to 150 mg/mL, 50 mg/mL to 150 mg/mL, 100 mg/mL to 150 mg/mL, 10 mg/mL to 100 mg/mL, 50 mg/mL to 100 mg/mL, 10 mg/mL to 50 mg/mL or any range between these ranges.

In accordance with this aspect of the present invention, the incorporation of one or more PFA surfactants in a pharmaceutical formulation containing a therapeutic protein that was produced in a biological system, like a cell, is particularly advantageous, because PFAs are resistant to degradation by residual host cell proteins that are carried over to the formulation. In particular, PFAs are resistant to host cell lipases that are not, and cannot be, adequately removed from the therapeutic protein preparation, and which are highly active at very low concentrations (≥1 unit/mL of purified porcine esterase or equivalent thereof). As described supra, suitable PFA surfactants have the general structure of Formula I. In one embodiment, the length of the hydrophilic ethylene oxide chain comprises about 1 to about 40 units. In one embodiment, the length of the ethylene oxide chain comprises about 5 to about 40 ethylene oxide units.

In one embodiment, a polyoxyethylene lauryl ether, e.g., polyoxyethylene (23) lauryl ether (also known by the tradenames Brij® L23 and Brij® 35), is incorporated into the pharmaceutical formulation to reduce aggregate and/or particulate formation in the formulation. In another embodiment, a polyoxyethylene oleyl ether, e.g., polyoxyethylene (20) oleyl ether (also know by the tradenames Brij® 98 and Brij® 99) or polyoxyethylene (10) oleyl ether (also know by the tradenames Brij® O10 and Brij® 97), is incorporated into the pharmaceutical formulation to reduce aggregate and/or particulate formation in the formulation. In another embodiment, a polyoxyethylene cetyl ether, e.g., polyoxyethylene (20) cetyl ether (also known by the tradename Brij® 58), is incorporated into the pharmaceutical formulation to reduce aggregate and/or particulate formation in the formulation. In another embodiment, a polyoxyethylene stearyl ether, e.g., polyoxyethylene (20) stearyl ether (also know by the tradename Brij® S20), is incorporated into the pharmaceutical formulation to reduce aggregate and/or particulate formation in the formulation.

In one embodiment, the one or more PFA surfactants are incorporated into the pharmaceutical formulation such that the composition comprises 0.001% to about 0.4% (w/v) of PFA surfactant. In one embodiment, the method produces a pharmaceutical formulation comprising about 0.005% to about 0.2% (w/v) of PFA surfactant. In one embodiment, the method produces a pharmaceutical formulation comprising about 0.01% to about 0.1% (w/v) of PFA surfactant. In another embodiment, the method produces a pharmaceutical formulation comprising about 0.01% to about 0.09% (w/v) of PFA surfactant. In another embodiment, the method produces a pharmaceutical formulation comprising about 0.01% to about 0.06% (w/v) of PFA surfactant. In another embodiment, the method produces a pharmaceutical formulation comprising about 0.01% to about 0.04% (w/v) of PFA surfactant.

The methods of the present invention produce therapeutic protein pharmaceutical formulations having a stable surfactant concentration. In accordance with these methods, >90% of the PFA remains intact in the formulation after the formulation is stored at about 1° C. to about 10° C. for about six months, at least about 12 months, at least about 18 months, at least about 24 months, at least about 30 months, at least about 36 months, at least about 42 months, or at least about 48 months. In another embodiment, the methods of the present invention produce formulations where >95% of the PFA remains intact in the formulation after the formulation is stored at about 1° C. to about 10° C. for at least about six months, at least about 12 months, at least about 18 months, at least about 24 months, at least about 30 months, at least about 36 months, at least about 42 months, or at least about 48 months.

In another embodiment, the methods of the present invention produce formulations where >90% of the PFA remains intact after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months. In another embodiment, the methods of the present invention produce formulations where >95% of the PFA remains intact after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months.

In another embodiment, the methods of the present invention produce formulations where >90% of the PFA remains intact after the formulation is stored at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months. In another embodiment, the methods of the present invention produce formulations where >95% of the PFA remains intact after the formulation is stored at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months.

In another embodiment, the methods of the present invention produce stable therapeutic protein formulations where >90% of the therapeutic protein (e.g., antibody) is in a monomeric state after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months. In another embodiment, the methods of the present invention produce formulations where >95% of the therapeutic protein in the formulation is in a monomeric state after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months.

The methods of the present invention produce stable therapeutic protein pharmaceutical formulations where >90% of the therapeutic protein (e.g., antibody) is in a monomeric state after the formulation is stored at about 1° C. to about 10° C. for about six months, at least about 12 months, at least about 18 months, at least about 24 months, at least about 30 months, at least about 36 months, at least about 42 months, or at least about 48 months. In some embodiments, the methods described herein produce therapeutic protein formulations where >95% of the therapeutic protein is in a monomeric state after the formulation is stored at about 1° C. to about 10° C. for at least about six months, at least about 12 months, at least about 18 months, at least about 24 months, at least about 30 months, at least about 36 months, at least about 42 months, or at least about 48 months.

In another embodiment, the methods of the present invention produce formulations where >90% of the therapeutic protein (e.g., antibody) is in a monomeric state after the formulation is stored at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months. In another embodiment, the methods of the present invention produce formulations where >95% of the therapeutic protein is in a monomeric state after the formulation is stored at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months.

In another embodiment, the methods of the present invention produce stable formulations resistant to sub-visible particulate formation. In one embodiment, the formulations as described herein contain ≤6000 particles (≥10 μm in size) per container and ≤600 particles (≥25 μm in size) per container after storage at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months.

The methods of the present invention produce stable therapeutic protein pharmaceutical formulations resistance to sub-visible particulate formation during cold storage. In one embodiment, the methods produce formulations containing 6000 particles (≥10 μm in size) per container and ≤600 particles (≥25 μm in size) per container after storage at about 1° C. to about 10° C. for about six months, at least about 12 months, at least about 18 months, at least about 24 months, at least about 30 months, at least about 36 months, at least about 42 months, or at least about 48 months.

In another embodiment, the methods of the present invention produce stable therapeutic protein pharmaceutical formulations resistance to sub-visible particulate formation during long-term cold storage. In one embodiment, the methods described herein produce formulations containing ≤6000 particles (≥10 μm in size) per container and ≤600 particles (≥25 μm in size) per container after storage at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months.

In another embodiment, the methods of the present invention produce stable formulations resistant to visible particulate formation. In one embodiment, the methods produce formulations containing ≤80 particles (≥70 μm in size) per milliliter after storage at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months. In another embodiment, the methods described herein produce formulations containing ≤10 particles (≥70 μm in size) per milliliter after storage at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months.

The methods of the present invention produce stable therapeutic protein pharmaceutical formulations resistance to visible particulate formation during cold storage. In one embodiment, the methods described herein produce formulations containing ≤80 particles (≥70 μm in size) per milliliter after storage at about 1° C. to about 10° C. for about six months, at least about 12 months, at least about 18 months, at least about 24 months, at least about 30 months, at least about 36 months, at least about 42 months, or at least about 48 months. In another embodiment, the methods described herein produce formulations containing ≤10 particles (≥70 μm in size) per milliliter after storage at about 1° C. to about 10° C. for at least about six months, at least about 12 months, at least about 18 months, at least about 24 months, at least about 30 months, at least about 36 months, at least about 42 months, or at least about 48 months.

In another embodiment, the methods of the present invention produce stable therapeutic protein pharmaceutical formulations resistance to visible particulate formation during long-term cold storage. In one embodiment, the methods described herein produce formulations containing ≤80 particles (≥70 μm in size) per milliliter after storage at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months. In another embodiment, the methods described herein produce formulations containing ≤10 particles (≥70 μm in size) per milliliter after storage at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months.

In another embodiment, the methods of the present invention produce stable formulations with low turbidity. In one embodiment, the methods described herein produce formulations having ≤18.0 NTU (Nephelometric Turbidity Unit) after storage at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months.

The methods of the present invention produce stable therapeutic protein pharmaceutical formulations with low turbidity during cold storage. In one embodiment, the methods described herein produce formulations having ≤18.0 NTU after storage at about 1° C. to about 10° C. for about six months, at least about 12 months, at least about 18 months, at least about 24 months, at least about 30 months, at least about 36 months, at least about 42 months, or at least about 48 months.

In another embodiment, the methods of the present invention produce stable therapeutic protein pharmaceutical formulations having low turbidity during cold storage. In one embodiment, the turbidity of the formulations as described herein is ≤18.0 NTU after storage at about −15° C. to about −90° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months.

In another embodiment, the methods of the present invention produce pharmaceutical formulations where the shelf life of the formulation is extended at least about one month, at least about two months, at least about three months, at least about four months, at least about five months, at least about six months, at least about seven months, at least about eight months, at least about nine months, at least about ten months, at least about eleven months, or at least about twelve months beyond the shelf life of a corresponding formulation containing a polysorbate surfactant.

Having generally described the invention, the same will be more readily understood by reference to the following examples, which are provided by way of illustration and no way limit the scope of the invention.

EXAMPLES

Materials and Methods

Materials: Surfactants investigated in this study included PFA and polysorbates. Two PFA, Brij® 35 (L23) (Product #ET47399, CAS #9002-92-0) and Brij® 98 (O20) (Product #ET40118, CAS #9004-98-2), were obtained from Croda International PLC (East Yorkshire, UK). Polysorbate 20 (Product #4116-04, CAS #9005-64-5) and polysorbate 80 (Product #4117-03, CAS #9005-65-6) were obtained from JT Baker (Center Valley, Pennsylvania). Lipase immobilized on polystyrene beads at 2.0 U/mg (Product Number 73940) was obtained from Fluka (Denmark). All monoclonal antibodies (mAbs) were produced or acquired by Janssen Supply Chain, LLC (Horsham, Pennsylvania) and purified in a series of chromatography and filtration steps.

Size Exclusion Chromatography (SEC). The soluble aggregation quality attribute of the investigated formulations was evaluated using size exclusion ultra performance liquid chromatography (SE-UPLC). To prepare samples for analysis, collected formulations from each condition (time zero (T0) control, shaking stress, and thermal stress followed by shaking stress) were diluted with formulation buffer of each respective mAb from 50 mg/mL to 2 mg/mL. SEC runs were conducted with a 5 µL injection of sample into an Acquity UPLC 200 Å, 1.7 µm column using a 0.2 M sodium phosphate mobile phase. Eluting peaks were integrated to determine monomer content based on percent area of the main peak relative to sum of all peak areas.

Dynamic Light Scattering (DLS). Particulate formation was assessed using dynamic light scattering. To prepare samples for analysis, collected formulations from each condition (T0 control, shaking stress, and thermal stress followed by shaking stress) were diluted with formulation buffer of each respective mAb from 50 mg/mL to 2 mg/mL. Diluted samples were then measured using a DLS instrument at constant 20° C., with percent scattering intensity reported as a function of particle size range. Particle size bins included: 2-8 nm, 8-60 nm, 60-300 nm, and 300-10,000 nm.

Surfactant Quantitation. Surfactant quantitation of samples was performed using UPLC with evaporative light scattering detection. Duplicate 7.5 µL sample injections were injected into an OASIS MAX column (30 µm, 2.1×20 mm). The mobile phase consisted of a gradient of milliQ water and isopropanol with 2% formic acid. The integrated area for each sample's eluting peak was assessed against a surfactant standard curve created from serial dilution of each surfactant type ranging from 0.005% (w/v) to 0.08% (w/v).

Assay for esterase/lipase activity. The enzymatically catalyzed hydrolysis of 4-Nitrophenyl acetate (Sigma, Product No.: N8130) was used as a model system to measure esterase/lipase activity (Valkova, N., et al., "Purification and characterization of PrbA, a new esterase from *Enterobacter cloacae* hydrolyzing the esters of 4-hydroxybenzoic acid (Parabens)", *J. Biol. Chem.* 278(15), pp. 12779-12785 (2003), John, G. T., and Heinzle, E., "Quantitative screening method for hydrolases in microplates using pH indicators: determination of kinetic parameters by dynamic pH monitoring", *Biotechnol. Bioeng.* 72(6), pp. 620-627 (2001), which are hereby incorporated by reference in their entirety). In brief, the assay measures the conversion of 4-Nitrophenyl Acetate to 4-Nitrophenol by esterase/lipase. At pH>6, the 4-Nitrophenol is deprotonated (phenolate) and is colored yellow. The presence of phenolate is monitored at 400 nm and the intensity of the color is pH dependent from 6.0 to 8.0. To compensate for differences in formulation buffer pH, 25 mM HEPES buffer at pH=7.5 was used to adjust the pH to 7.0 prior to the assay. Controls for the assay included, NaOH, HCl, porcine esterase (Sigma Product No.: E2884-5KU), water, and formulation buffer without protein.

Example 1—PFA Surfactants Protect mAbs from Shaking and Thermal Stability Stresses To assess the protective effects of different surfactants in mAb formulations, polysorbate and PFA was spiked into formulations for three different mAbs. mAbs A and B are bispecific antibodies, and mAb C is an IgG4 monoclonal antibody. The formulations for mAbs A and B comprised 10 mM histidine, 8.5% (w/v) sucrose, at pH 5.7. The mAb C formulation consisted of 10 mM sodium phosphate, 8.5% (w/v) sucrose, 10 ppm EDTA, at pH 7.1. All three mAbs were at a 50 mg/mL concentration in their respective formulations. Stock 3% (w/v) surfactant solutions were spiked into the mAb formulations to yield 0.01% and 0.04% (w/v) polysorbate or PFA concentrations in each mAb's final formulation. After each formulation was prepared, the material was filled into autoclaved 2R glass vials with a 1 mL fill, stoppered, and crimp sealed. These vialed formulations were then divided into three conditions: T0 control, shaking stress (72 hours on an orbital shaker at 250 RPM in ambient temperature), and thermal stress (3-month incubation at 25° C.) followed by shaking stress (72 h at 250 RPM). Each formulation condition was evaluated with vials in triplicate. The impact of the surfactant type and concentration was assessed using size exclusion chromatography (SEC).

Figure 1B:
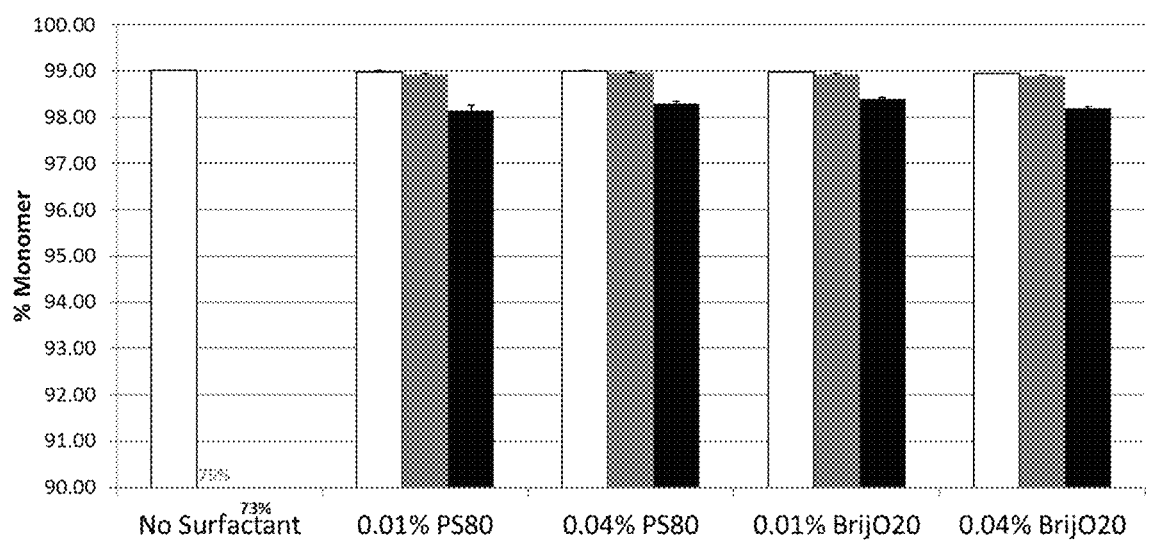
Figure 1C:
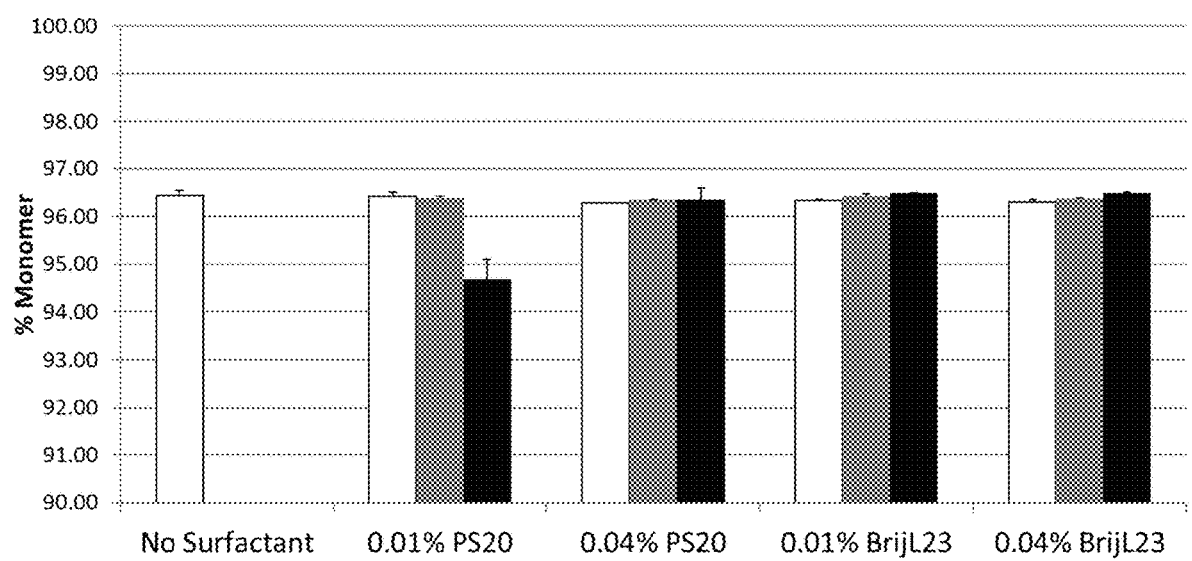

FIGS. 1A-1C are graphs showing the percentage of each formulation that is in the desired monomeric state as assessed by SEC. The comparison of polysorbate and PFA containing formulations reveals similar percent monomer results when formulations are exposed to shaking and thermal stresses. At the low 0.01% (w/v) surfactant level, SEC results indicate that PFA (Brij O20 and Brij L23) formulations retain higher percent monomer content than polysorbate (PS20 and PS80) formulations for the stressed condition of 3-month storage at 25° C. following by shaking stress (Student's t-test, p<0.01). These findings suggest PFA formulations may be able to provide more protection against thermal and shaking stresses than polysorbate at low concentrations.

Example 2—PFA Sock Solutions Exposed to Lipases Immobilized on Beads Exhibit Significant Resistance to Degradation Stock solutions of PFA and polysorbate surfactants were exposed to lipases immobilized on beads over a period of 18 days. Surfactant levels in the solutions were quantified periodically over the course of testing to determine the extent of lipase-mediated degradation.

The quantitation of intact polysorbate levels in solutions exposed to lipases suggested a >50% reduction of intact polysorbate content after 3 days (see FIG. 2). In contrast, the PFA surfactant levels remained essentially unchanged for the entire duration of exposure, up to 18 days (FIG. 2). These results highlight the difference in resistance to lipase-mediated degradation of PFA versus polysorbate, and demonstrate that PFA surfactants would remain intact in mAb formulations despite residual host cell proteins from the antibody manufacturing process.

Example 3—mAb Stability is Maintained in Formulations Containing PFA Surfactant Exposed to Lipase Further studies evaluated the ability of PFA and polysorbate formulations to retain their protective effects after exposures of the surfactants to lipase. The mAb formulations were spiked with surfactants that had been exposed to lipase-beads and then subjected to shaking stress or thermal stress followed by shaking. The mAb formulations were then evaluated for soluble aggregation and particulate matter using SEC and DLS, respectively.

Figure 3A:
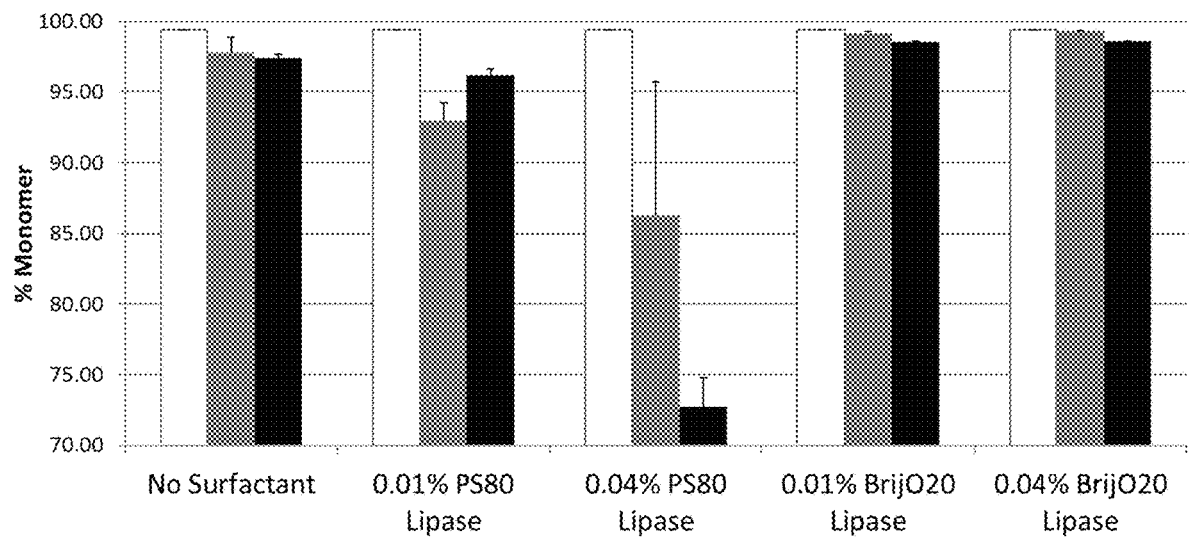
FIGS. 3A-3C are graphs showing the protective effects of polysorbate and PFA surfactants in three different antibody formulations following lipase exposure of the surfactants as assessed by SEC. Antibody stability was assessed based on percent monomer present in each formulation at T0 (white bars), after shaking stress (72 hours of shaking at 250 RPM at ambient temperature) (grey bars), and after thermal stress (3 month incubation at 25° C., followed by shaking stress of 72 h at 250 RPM) (black bars). The three antibody formulations that were tested include bispecific mAb A (FIG. 3A), bispecific mAb B (FIG. 3B), and IgG4 mAb C (FIG. 3C).
Figure 3B:
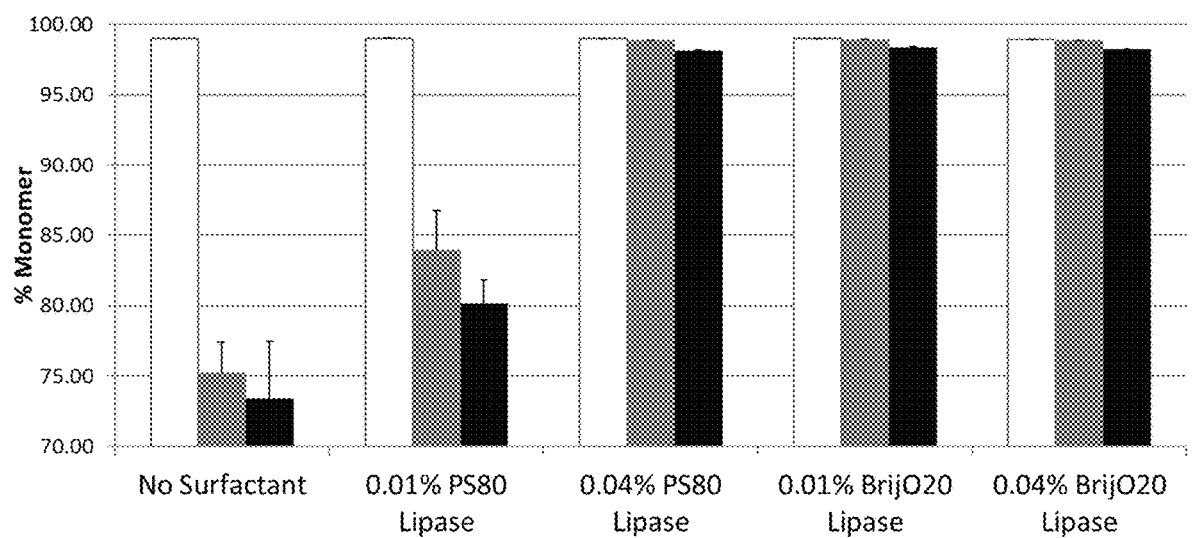
Figure 3C:
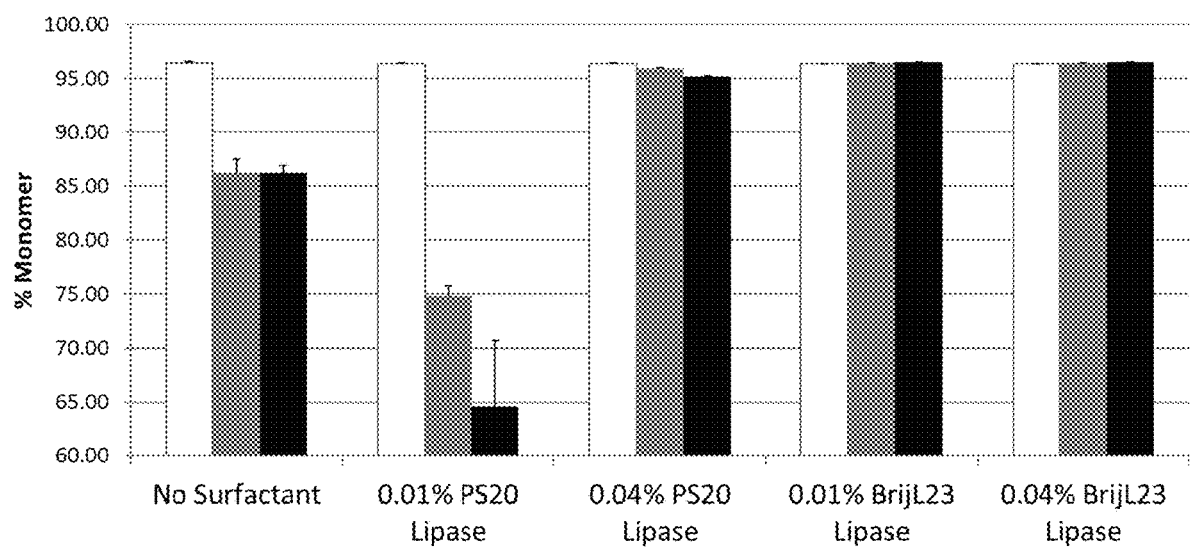

The SEC results demonstrate the deleterious effects of lipase exposure on polysorbate surfactants and the associated impact on mAb stability. In some cases, the presence of polysorbate exposed to lipase resulted in lower percent monomer content than control formulations without any surfactant (see FIG. 3A, compare 0.01% PS80 and 0.04% PS80 to No Surfactant, and FIG. 3C, compare 0.01% PS20 to No Surfactant). This highlights the disadvantage of using polysorbate surfactants in formulation circumstances involving lipase exposure. By contrast, across each investigated mAb, the PFA formulations retained their protective effects despite lipase exposure. At 0.01% (w/v) surfactant level, PFA formulations of each mAb outperform polysorbate formulations and no surfactant controls for all stress conditions. At the higher 0.04% (w/v) surfactant level, certain mAbs do not exhibit a strong decrease in soluble aggregate as measured by SEC, but the detrimental effect of lipase-mediated polysorbate degradation is instead evident by insoluble particulate formation.

Figure 4A:
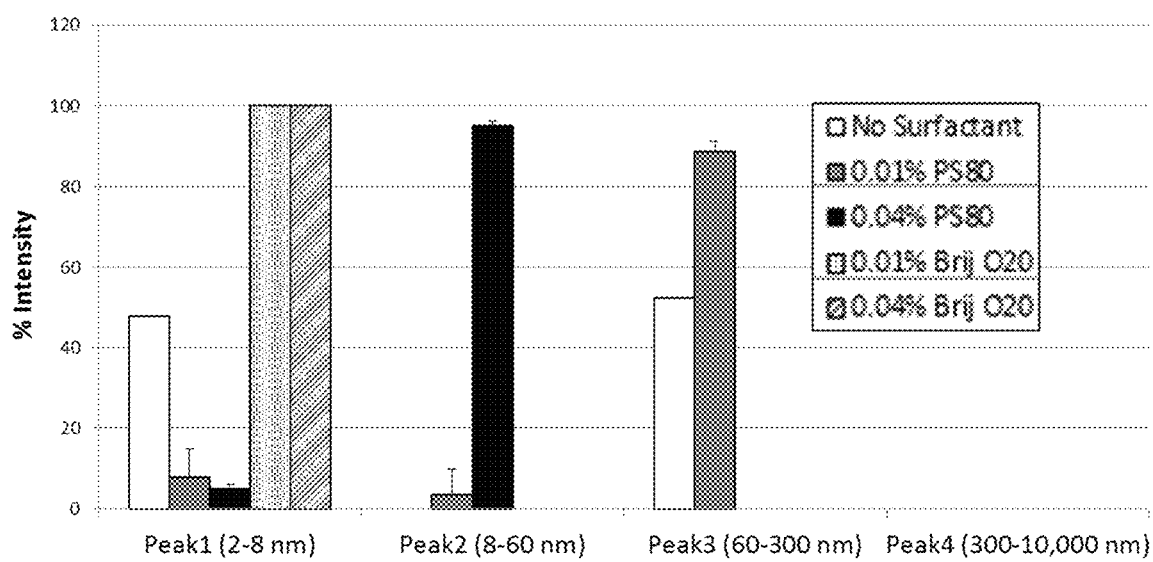
FIGS. 4A-4C are graphs showing the protective effects of polysorbate and PFA surfactants in three different antibody formulations following lipase exposure of the surfactants as assessed by dynamic light scattering (DLS). DLS analysis was used to measure particle size distribution in each antibody formulation after thermal stress (3 months at 25° C. and shaking 72 hours at 250 RPM). Particles binning to peak 1 (2-8 nm) represent monomers, while particles in peaks 2 to peak 4 represent larger particulate ranging from 8 nm to 10,000 nm, which are indicative of aggregates.
Figure 4B:
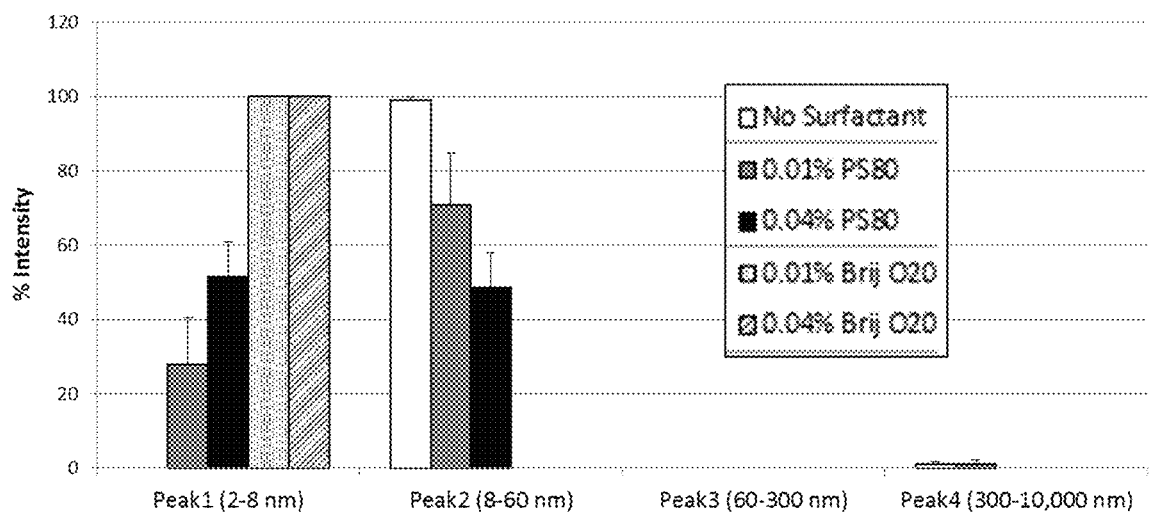
Figure 4C:
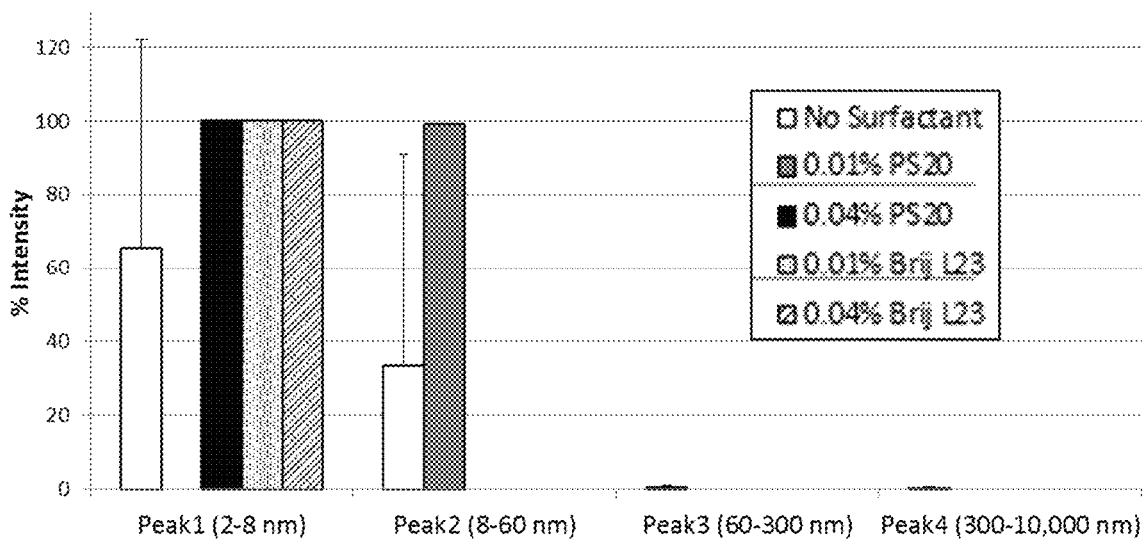

The impact of lipase exposure on formulation stability was also demonstrated in orthogonal assays such as DLS which evaluate particulate formation as a function of surfactant. The DLS particle size distribution results show that polysorbate formulations exposed to lipases are more prone to larger size particulate formation than PFA formulations (see FIGS. 4A-4C). For both low and high surfactant level, essentially all the scattering intensity in PFA formulations derives from particle sizes binned in peak 1, which correlates to a monomer size range. This contrasts to the polysorbate formulations, which have a significant amount of scattering derived from larger particulates ranging from 8 nm to 300 nm (FIGS. 4A-4B).

The orthogonal DLS assay complements SEC results and demonstrates that PFA formulations outperform polysorbate formulations in their ability to protect the mAb from soluble aggregation and insoluble particulate formation in conditions where lipases can degrade ester bond containing surfactants.

Figure 5:
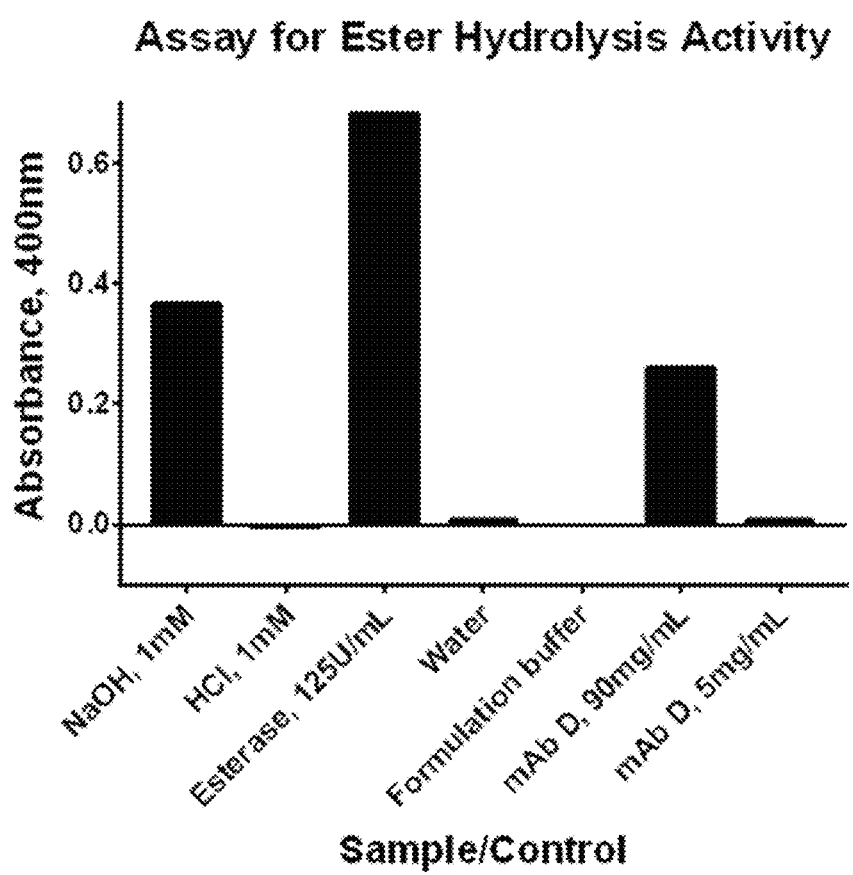
FIG. 5 is a graph showing esterase/lipase activity in mAb D formulations with concentrations of 90 mg/ml and 5 mg/ml. Controls for the assay included, NaOH, HCl, porcine esterase (Sigma Product No.: E2884-5KU), water, and formulation buffer without protein.

Example 4—an Esterase/Lipase Activity Level ≥1 Units/mL is Detrimental to Therapeutic Protein Formulations To determine the threshold level of host cell derived esterase/lipase activity that is detrimental to a therapeutic protein formulation, esterase/lipase activity was determined in formulations containing different concentrations of purified therapeutic proteins (antibodies). A representative example is shown in FIG. 5, with analysis of esterase/lipase activity in mAb D formulations with concentrations of 90 mg/ml and 5 mg/ml. As shown in FIG. 5, mAb D formulations containing 5 mg/mL total protein exhibited a lower level of esterase/lipase activity (see last bar in graph of FIG. 5). While this level of esterase/lipase activity was detectable and the effects measurable, it was determined that esterase/lipase activity below this level of activity could be acceptable with regard to polysorbate degradation and stability of a therapeutic protein. Thus, the esterase/lipase activity below what is present in the 5 mg/mL sample of mAb D was determined to be an acceptable esterase/lipase activity level. A more prudent cutoff for an acceptable level of esterase/lipase activity would be activity that is <10% of the activity present in the 5 mg/mL sample of mAb D.

Data analysis determined that the esterase/lipase activity in the 5 mg/mL mAb D sample represented 1% of the esterase control (porcine esterase; Sigma PN E2884-5KU, CAS #9016-18-6, EC3.1.1.1) having 125 U/mL activity. Based on that analysis, an acceptable level of esterase/lipase activity in the mAb D formulation corresponds to <1.25 Units/mL of porcine esterase. Rounding to the correct number of significant figures, an acceptable level of esterase/lipase activity in the mAb D formulation corresponds to <1 Units/mL of porcine esterase. In certain embodiments, an acceptable level of esterase/lipase activity in the mAb D formulation corresponds to <1, <0.9, <0.8, <0.7, <0.6, <0.5, <0.4, <0.3, <0.2, or <0.1 Units/mL of porcine esterase. In certain embodiments, an acceptable level of esterase/lipase activity in the mAb D formulation corresponds to <0.1 Units/mL of porcine esterase. Thus, an esterase/lipase activity level corresponding to ≥1 Units/mL of porcine esterase is considered to be detrimental to a therapeutic protein formulation. In certain other embodiments, esterase/lipase activity level corresponding to ≥1, ≥0.9, ≥0.8, ≥0.7, ≥0.6, ≥0.5, ≥0.4, ≥0.3, ≥0.2, or ≥0.1 Units/mL of porcine esterase is considered to be detrimental to a therapeutic protein formulation. In certain other embodiments, esterase/lipase activity level corresponding to ≥0.1 Units/mL of porcine esterase is considered to be detrimental to a therapeutic protein formulation. According to the data presented herein, a polysorbate surfactant may not be the best choice for a formulation with an esterase/lipase activity level corresponding to ≥1 Units/mL of porcine esterase. In certain other embodiments, a polysorbate surfactant may not be the best choice for a formulation with an esterase/lipase activity level corresponding to ≥1, ≥0.9, ≥0.8, ≥0.7, ≥0.6, ≥0.5, ≥0.4, ≥0.3, ≥0.2, or ≥0.1 Units/mL of porcine. Rather, the data suggests that polysorbate surfactants should be avoided in formulations with an esterase/lipase activity level corresponding to ≥1 Units/mL of porcine esterase. In addition, the data suggests that polysorbate surfactants should be avoided in formulations with an esterase/lipase activity level corresponding to ≥1, ≥0.9, ≥0.8, ≥0.7, ≥0.6, ≥0.5, ≥0.4, ≥0.3, ≥0.2, or ≥0.1 Units/mL of porcine esterase. In certain other embodiments, polysorbate surfactants should be avoided in formulations with an esterase/lipase activity level corresponding to ≥0.1 Units/mL of porcine esterase. Instead, a polyethoxylated fatty alcohol surfactant as described herein should be used in a formulation with an esterase/lipase activity level corresponding to ≥1 Units/mL of porcine esterase. In certain other embodiments, a polyethoxylated fatty alcohol surfactant as described herein should be used in a formulation with an esterase/lipase activity level corresponding to ≥1, ≥0.9, ≥0.8, ≥0.7, ≥0.6, ≥0.5, ≥0.4, ≥0.3, ≥0.2, or ≥0.1 Units/mL of porcine esterase. In certain other embodiments, a polyethoxylated fatty alcohol surfactant as described herein should be used in a formulation with an esterase/lipase activity level corresponding to ≥0.1 Units/mL of porcine esterase.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A biological composition comprising:
   about 20 mg/mL to about 200 mg/mL of a protein;
   a pharmaceutically acceptable carrier; and
   one or more polyethoxylated fatty alcohol (PFA) surfactants, wherein said one or more PFA surfactants is resistant to lipase degradation,
   wherein said biological composition comprises a lipase/esterase activity that is ≥0.1 unit/mL of purified porcine esterase, and
   wherein the protein is a non-recombinant, serum isolated protein, or a recombinant protein, wherein the protein was produced in a cell line selected from the group consisting of Chinese hamster ovary (CHO) cell line, PER.C6 cell line, and Sp2/0 cell line.

2. The biological composition of claim 1, wherein the concentration of the protein in the composition is about 50 mg/mL to about 150 mg/mL.

3. The biological composition of claim 1, wherein the one or more PFA surfactants comprise a PFA having between 5 to 40 ethylene glycol units.

4. The biological composition of claim 3, wherein the one or more PFA surfactants is polyoxyethylene (23) lauryl ether and/or polyoxyethylene (20) oleyl ether.

5. The biological composition of claim 1, wherein the PFA surfactant concentration in the composition is about 0.005% to about 0.2% (w/v).

6. The biological composition of claim 1, wherein the composition comprises lipase/esterase activity that is ≥1 unit/mL of purified porcine esterase or equivalent thereof.

7. The biological composition of claim 1, wherein >90% the PFA surfactant remains intact in the composition over the composition's shelf life.

8. The biological composition of claim 1 further comprising:
   a saccharide, said saccharide comprising about 0.5% to 15% w/v of the composition; and,
   buffering salts in a concentration of about 5 mM to 50 mM.

9. The biological composition of claim 1, wherein said composition has a pH of between 5-8.

10. The biological composition of claim 1, wherein the composition is resistant to particulate formation.

11. The biological composition of claim 10, wherein the composition contains ≤80 particle/mL of particles having an equivalent circular diameter of ≥70 µm over composition's shelf life.

12. The biological composition of claim 10, wherein the composition contains ≤6000 particles (≥10 µm in size) per container and ≤600 particles (≥25 µm in size) per container over the composition's shelf life.

13. The biological composition of claim 1, wherein the composition is resistant to protein aggregation.

14. The biological composition of claim 13, wherein >90% of the protein in the composition is in a non-aggregated state over the composition's shelf life.

* * * * *